US00PP21348P2

(12) United States Plant Patent
Lehman

(10) Patent No.: US PP21,348 P2
(45) Date of Patent: Sep. 28, 2010

(54) KENTUCKY BLUEGRASS PLANT NAMED 'B-5.0815'

(50) Latin Name: ***Poa pratensis* L.**
Varietal Denomination: B-5.0815

(76) Inventor: Virginia Lehman, PO Box 2390, Lebanon, OR (US) 97355

( * ) Notice: Subject to any disclaimer, the term of this patent is extended or adjusted under 35 U.S.C. 154(b) by 0 days.

(21) Appl. No.: 12/383,271

(22) Filed: Mar. 23, 2009

(51) Int. Cl.
*A01H 5/00* (2006.01)

(52) U.S. Cl. ..... Plt./393

(58) Field of Classification Search ..... Plt./393

See application file for complete search history.

(56) References Cited

U.S. PATENT DOCUMENTS

PP9,036 P * 1/1995 Meier et al. ..... Plt./393
PP11,536 P * 10/2000 Meier et al. ..... Plt./393

OTHER PUBLICATIONS

U.S. Plant Variety Protection 9100128. 'Gunger' Kentucky bluegrass.*
US Plant Variety Protection 7200117. 'Baron' Kentucky bluegrass.*
Olson, G.L., S.R. Smith, G.D. Lace Field, and T. D. Philips. Timothy and Kentucky bluegrass report. 2008. Pr-575. Agricultural Experiment Station, Univ. & Kentucky. College of Agriculture, Lexington, KY. 40546.*

* cited by examiner

*Primary Examiner*—Susan B McCormick Ewoldt

(57) ABSTRACT

A variety of Kentucky bluegrass produced vegetatively by rhizomes, tillers and apomictic caryopses, distinguished by a unique combination of characters including coarse leaf blade width and high dry matter yield under grazing.

1 Drawing Sheet

Figure 1:
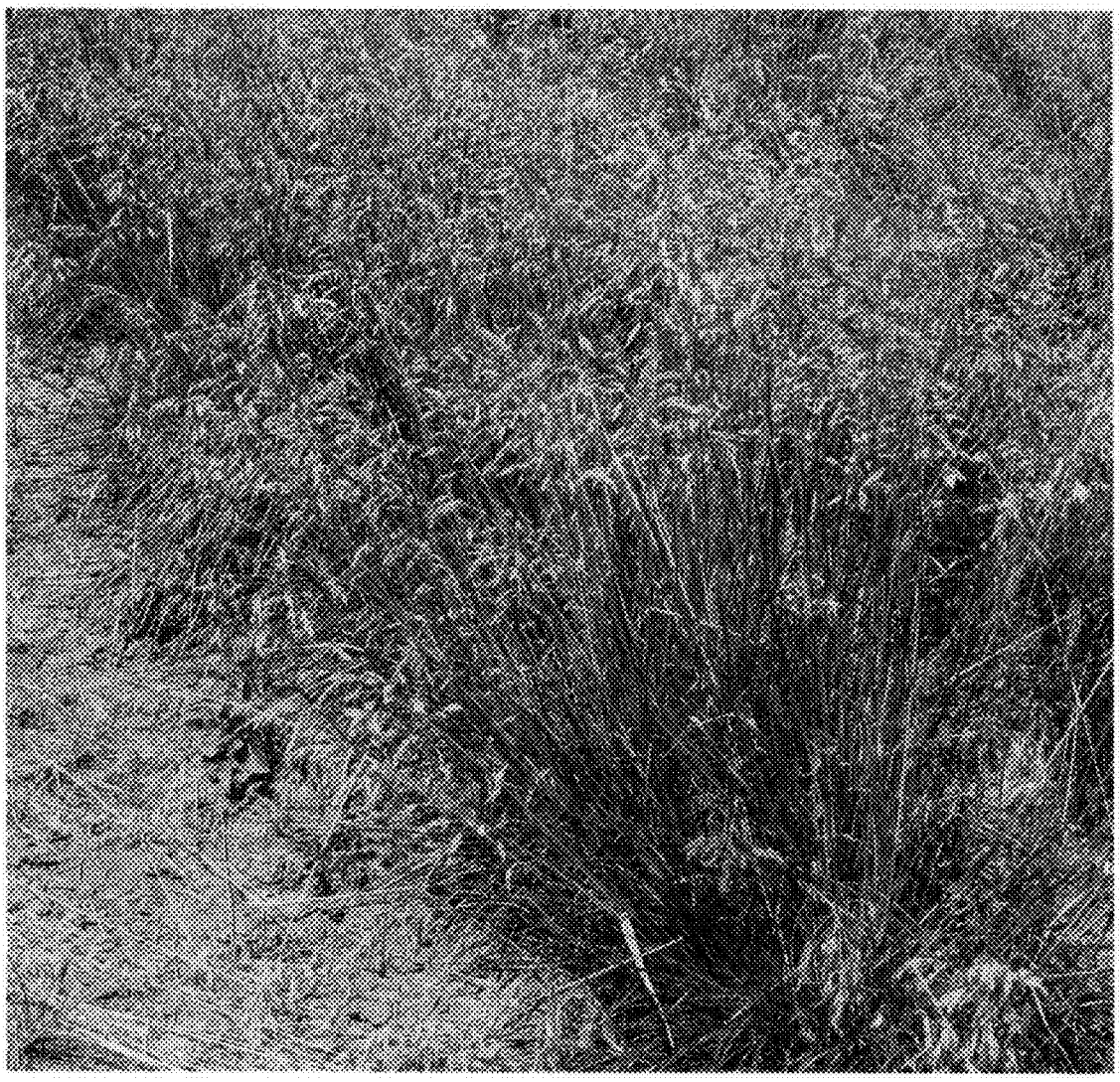

Latin name of the genus and species of the plant claimed: The present invention relates to the genus and species *Poa pratensis* L.

Variety denomination: 'B-5.0815'.

Field of invention: The present invention relates to a new and distinct asexually reproduced variety of perennial *Poa pratensis* L.

BACKGROUND OF THE INVENTION

This invention relates to a new and distinct perennial *Poa pratensis* L. cultivar identified as 'B-5.0815' Kentucky bluegrass (herein referred to as 'B-5.0815'). The inventor, Virginia G. Lehman, discovered 'B-5.0815' under cultivated conditions in a planting of Kentucky bluegrass seedlings near Lebanon, OR. 'B-5.0815' was identified as a distinctly different vegetative segregated clonal plant differing by much higher tiller density and forage production than the surrounding plants. The inventor asexually reproduced 'B-5.0815' by taking vegetative cuttings of the plant material from the plant including rhizomes and tillers, cutting the rhizomes into segments, each with a vegetative bud, and rooting them in pots in a greenhouse near Lebanon, Oreg. Vegetative plugs of 'B-5.0815' were asexually reproduced and moved to field nurseries of near Lebanon, OR for further evaluation.

For purposes of registration under the "International Convention for the Protection of New Varieties of Plants" (generally known by its French acronym as the UPOV Convention) and noting Section 1612 of the Manual of Plant Examining Procedure, it is proposed that the title of the invention is Kentucky bluegrass plant named 'B-5.0815'.

BRIEF DESCRIPTIONS OF THE ILLUSTRATIONS

FIG. 1 is a photograph of 'B-5.0815' Kentucky bluegrass plant in the reproductive phase in the field.

COMPLETE DESCRIPTION OF THE VARIETY

'B-5.0815' was characterized in greenhouse and field conditions. 'B-5.0815' is a unique variety of Kentucky bluegrass (*Poa pratensis* L.) that was discovered under cultivated conditions in a field nursery of Kentucky bluegrasses planted from seed. 'B-5.0815' originated as an open pollinated progeny with 'B-99.1435' as the seed parent. 'B-99.1435' is an unpatented, unreleased, Kentucky bluegrass plant grown and maintained in the plant nursery near Lebanon, Oreg., and whose parents are unknown. 'B-5.0815' was identified as having a much higher leaf production than the surrounding Kentucky bluegrasses. The field nursery was located in USDA Plant Hardiness Zone 8b. 'B-5.0815' was propagated by the inventor under field and greenhouse conditions in Lebanon, Oreg. by cutting of rhizomes and tillers, rooting them in soil, and planting of the rooted material to provide planting stock for studying performance and for comparison of morphological characters after propagation. 'B-5.0815' has been propagated by stolons, tillers, and apomictic caryopses. Asexually reproduced plants of 'B-5.0815' from stolons, tillers, and apomictic caryopses have remained stable and true to type indistinguishable from the mother plant through successive generations of propagation. The apomixes level of 'B-5.0815' is approximately 90%.

'B-5.0815' is a perennial Kentucky bluegrass that spreads by rhizomes, tillers, and caryopses. Characteristics of 'B-5.0815' measured in 2008 were taken from plants that were approximately 20 months in age grown on a Malabon Silty clay loam with pH of 6.8.

'B-5.0815' has a shorter plant height than 'Kenblue' (not patented) and is taller than 'Baron' (US Plant Variety Protection 7200117) (Table 1) when measured under field conditions in Lebanon, Oreg., 2008. 'B-5.0815' has a wider flag leaf width than 'Kenblue' (Table 1). The inflorescences of 'B-5.0815' produced in the field have panicle lengths of 12.2 cm compared to the significantly shorter panicle of 'Baron' (8.9 cm). The combination of characters of earlier heading than Baron, long panicle length not different from Kenblue, and a wider leaf blade than both 'Kenblue' and 'Baron' distinguish 'B-5.0815'. 'B-5.0815' has retained the unique characters during successive stages of propagation and has shown to be a stable variety in asexual propagation.

'B-5.0815' has shown susceptibility to stripe rust (*Puccinia striiformis* Westend.) in tests near Lebanon, Oreg. 'B-5.0815' has shown similar dry matter yield in trials in Lexington, Ky. (Table 2) compared to 'Kenblue' and 'Ginger' (US Plant Variety Protection 9100128) when tested in 2007 and 2008. 'B-5.0815' is adapted North/South from the Kentucky border through Canada, and East/West from Kentucky to Oregon. 'B-5.0815' is similar to most Kentucky bluegrasses in performance with recovery from plant stress from rhizomes. 'B-5.0815' is adapted from sandy to heavier loam soil textures and from slightly acid to slightly alkaline soil pH.

TABLE 1

Morphological characteristics of selected bluegrass cultivars, measured under field conditions in Lebanon, OR, 2008.

| Name | Heading Date (Julian) | Date of Flower (Julian) | Panicle Length (cm) | Flag Leaf Height (cm) | Flag Leaf Length (cm) |
|---|---|---|---|---|---|
| 'Kenblue' | 75 | 130 | 13.3 | 49.3 | 6.9 |
| 'Baron' | 124 | 140 | 8.9 | 35.4 | 5.3 |
| 'B-5.0815' | 119 | 142 | 12.2 | 54.5 | 9.7 |
| LSD, p = 0.05 | 2.36 | 2.58 | 1.62 | 7.83 | 1.95 |

| Name | Flag Leaf Width (mm) | Sheath Length (cm) | panicle branch number | leaf number | Plant Height (cm) |
|---|---|---|---|---|---|
| 'Kenblue' | 3.3 | 37.1 | 5.4 | 3.3 | 94.5 |
| 'Baron' | 5.3 | 38.6 | 5.0 | 3.7 | 62.0 |
| 'B-5.0815' | 6.9 | 36.9 | 4.9 | 3.7 | 80.7 |
| LSD, p = 0.05 | 1.03 | ns | ns | ns | 9.07 |

TABLE 2

Dry matter yields of Kentucky bluegrass varieties sown 6 Sep. 2006 at Lexington, KY.

| Variety | Yield, tons/acre 2007 | Yield, tons/acre 2008 | 2-year total |
|---|---|---|---|
| 'Kenblue' | 1.62 | 2.08 | 3.70 |
| 'Ginger' | 1.47 | 2.06 | 3.53 |
| 'B-5.0815' | 1.72 | 1.64 | 3.36 |
| 'Common' | 0.70 | 0.78 | 1.48 |
| Lsd, p = 0.05 | 0.33 | 0.68 | 0.70 |

COMPLETE BOTANICAL DESCRIPTION OF THE VARIETY

Origin: 'B-5.0815' is a cultivar of a single vegetative clone of Kentucky bluegrass discovered under cultivated conditions in a planting of Kentucky bluegrasses planted near Lebanon, Oreg.

Classification: *Poa pratensis* L.

Growth habit: 'B-5.0815' is a perennial plant that spreads by rhizomes, tillers, and apomictic caryopses. 'B-5.0815' produces a large leafy plant with a highly fibrous root system.

The inflorescence of 'B-5.0815' is a panicle with some red purple 59A (based on Royal Horticultural Society Colour Chart) coloring in the panicle at 50% flowering.

Spikelet characters:

*Spikelet length in lowest whorl.*—3.2 mm.
*Spikelet width in lowest whorl.*—1.5 mm.
*Floret number in lowest whorl.*—2.
*Upper floret length in lowest whorl.*—2.7 mm.
*Upper floret width in lowest whorl.*—0.63 mm.
*Lower floret length in lowest whorl.*—2.9 mm.
*Lower floret width in lowest whorl.*—0.63 mm.
*Outer glume length of spikelet in lowest whorl.*—2.75 mm.
*Inner glume length of spikelet in lowest whorl.*—2.2 mm.
*Spikelet length in third whorl.*—4.35 mm.
*Spikelet width in third whorl.*—2.3 mm.
*Floret number in third whorl.*—2.3.
*Upper floret length in third whorl.*—3.0 mm.
*Upper floret width in third whorl.*—0.75 mm.
*Lower floret length in third whorl.*—3.4 mm.
*Lower floret width in third whorl.*—0.78 mm.
*Outer glume length of spikelet in third whorl.*—2.9 mm.
*Inner glume length of spikelet in third whorl.*—3.25 mm.
*Floret color at early heading.*—139C green with some greyed-purple 187B.

Inflorescence characters:

*Panicle length.*—12.2 cm.
*Flag leaf length.*—9.7 cm.
*Flag leaf width.*—6.8 mm.
*Branches per panicle.*—4.9.
*Panicle habit.*—Upright.
*Panicle type.*—Open.

Mature plant height, including inflorescence: 'B-5.0815': 80.7 cm; 'Baron': 62 cm. Color Notations, vegetative characters, based on The R.H.S. Colour Chart (light quality, photoperiod, and general growth of the plants affect color notations):

Leaf blade: folded in the bud, coarse compared to other Kentucky bluegrasses.

*Leaf blade color upper leaf surface.*—'B-5.0815':137B green; 'Baron': 137A green; 'Kenblue': 137A green.
*Leaf blade color lower leaf surface.*—'B-5.0815':137B green; 'Baron': 137A green; 'Kenblue': 137A green.
*Leaf blade texture rating.*—'B-5.0815'=coarse; 'Baron': medium; 'Kenblue': fine.

Apomictic caryopses description: Caryopses (seed) weight of 1000 caryopses: 0.3320 g.

*Caryopses weight class.*—'B-5.0815'=medium where light='Sydsport' (unpatented) and 'Merton' (unpatented) and where heavy='Fylking' (unpatented) or 'Nugget' (unpatented).
*Width.*—'B-5.0815'=0.6 mm.
*Length.*—'B-5.0815'=2.75 mm.
*Keel shape.*—Sharp.
*Palea.*—Strong hairs, teeth-like in character.
*Overall shape.*—Compressed.
*Lemma.*—Curls into seed, covering palea, papery in texture.
*Hairs.*—Present on lemma, on keel, and near rachilla, somewhat similar to *Poa trivialis.*
*Rachilla.*—Conical tapered tubular shape, similar to a golf tee.

What is claimed is:

1. A new and distinct variety of Kentucky bluegrass plant, substantially as described and illustrated herein, characterized particularly by a high dry matter forage yield and a coarse leaf texture.

* * * * *